(12) United States Patent
Hosokawa

(10) Patent No.: US 6,836,373 B2
(45) Date of Patent: Dec. 28, 2004

(54) SPHERICAL ABERRATION CORRECTOR FOR ELECTRON MICROSCOPE

(75) Inventor: Fumio Hosokawa, Tokyo (JP)

(73) Assignee: Jeol Ltd., Tokyo (JP)

( * ) Notice: Subject to any disclaimer, the term of this patent is extended or adjusted under 35 U.S.C. 154(b) by 144 days.

(21) Appl. No.: 10/194,412

(22) Filed: Jul. 12, 2002

(65) Prior Publication Data

US 2003/0029999 A1 Feb. 13, 2003

(30) Foreign Application Priority Data

Nov. 16, 2000 (JP) .................................... 2000-349222
Jul. 13, 2001 (JP) .................................... 2001-213697

(51) Int. Cl.[7] .................................................. G02B 21/02
(52) U.S. Cl. ................................. 359/659; 250/311
(58) Field of Search .............................. 359/369, 280, 359/656, 660; 250/311

(56) References Cited

U.S. PATENT DOCUMENTS

| 4,962,313 A | 10/1990 | Rose ........................ 250/311 |
| 5,084,622 A | 1/1992 | Rose ..................... 250/396 R |
| 6,191,423 B1 * | 2/2001 | Krijn et al. ............. 250/396 R |
| 6,329,659 B1 * | 12/2001 | Krijn et al. ............. 250/396 R |
| 6,555,818 B1 * | 4/2003 | Hosokawa .................. 250/311 |

OTHER PUBLICATIONS

Moore, John, Encyclepedia of Chemical Physics asnd Physical Chemistry, 2001,, Institute of Physics Publishing.*
"Correction of the spherical aberration of a 200kV TEM by means of a Hexapole–corrector", M. Haider et al., *Optik*, vol. 99, No. 4 (1995), pp. 167–179.

* cited by examiner

Primary Examiner—Georgia Epps
Assistant Examiner—Darryl J. Collins
(74) Attorney, Agent, or Firm—Webb Ziesenheim Logsdon Orkin & Hanson, P.C.

(57) ABSTRACT

A spherical aberration corrector used in an electron microscope. The corrector has a spherical aberration correction optical system that permits the magnification to be varied. Rotational relation between two multipole elements within a plane perpendicular to the optical axis can be corrected without varying the phase angles of the multipole elements. A rotation-correcting lens is positioned within the focal plane of an electron trajectory formed between two axially symmetric lenses in the corrector to rotate electrons within a plane perpendicular to the optical axis.

3 Claims, 3 Drawing Sheets f: FOCAL LENGTH   K: INTENSITY   Z: SIZE $f_1$, $f_2$: FOCAL LENGTH   $K_1$, $K_2$: INTENSITY   $Z_1$, $Z_2$: SIZE f: FOCAL LENGTH   K: INTENSITY   Z: SIZE $f_1, f_2$: FOCAL LENGTH   $K_1, K_2$: INTENSITY   $Z_1, Z_2$: SIZE

SPHERICAL ABERRATION CORRECTOR FOR ELECTRON MICROSCOPE

BACKGROUND OF THE INVENTION

1. Field of the Invention

The present invention relates to a spherical aberration corrector for use in an electron microscope.

2. Description of Related Art

In a known aberration corrector for correcting spherical aberration in lenses included in an electron microscope, two axially symmetric lenses are placed between two multipole elements that produce hexapole fields. Note that the "axially symmetric lens" is so designed that the geometrical arrangement of lens properties is not affected by rotation of the lens about the optical axis. FIG. 3 schematically shows the configuration of the illumination system of an electron microscope fitted with the conventional spherical aberration corrector. Note that the deflection system and a part of the focusing system are omitted from this figure. The microscope has a source 1 emitting an electron beam 2. This beam 2 passes through a condenser lens 4 having an aperture 3. The beam made parallel to the optical axis enters spherical aberration correction optics 5. An electron beam exiting from the correction optics 5 and traveling parallel to the optical axis is directed onto a specimen 7 through an objective lens 6.

The spherical aberration correction optics 5 comprise multipole elements 8 and 9 for producing the hexapole fields, and axially symmetric lenses 10 and 11 located between the multipole elements 8 and 9. These multipole elements 8 and 9 are so arranged that they are in phase with respect to the optical axis and have no rotational relation about the optical axis within a plane perpendicular to the optical axis. The lenses 10 and 11 have the same focal length of f. Their spherical aberration is corrected provided that the distance between the multipole element 8 and the axially symmetric lens 10 is f, the distance between the lenses 10 and 11 is 2 f, the distance between the lens 11 and the multipole lens 9 is f, the multipole elements 8 and 9 are excited with the same intensity K, and the elements 8 and 9 have the same width Z as measured along the optical axis.

With the conventional spherical aberration correction optics, however, it is necessary to realize certain arrangement conditions using axially symmetric lenses of the same focal length. Therefore, it is impossible to vary the magnification by means of the correction optics. Accordingly, the obtained minimum electron probe is limited by spherical aberration. Consequently, it is impossible to obtain a sufficiently small electron probe having a sufficient amount of current. The demagnifying action on the electron probe needs to be assigned to other lenses.

Furthermore, the multipole elements 8 and 9 need to be so arranged that there is no rotational relation about the optical axis within a plane perpendicular to the optical axis. In practice, a certain degree of rotational relation is inevitably introduced within manufacturing and assembly tolerances. In addition, electrons transmitted through the axially symmetric lenses 10 and 11 undergo a rotating action within the plane perpendicular to the optical axis. If the polarity of any coil is reversed, a certain degree of rotational relation is unavoidably introduced. Therefore, it is necessary to correct the introduced rotational relation by controlling the excitation of the multipole elements and rotating the phase angle of the acting field. Where the multipole elements are used in this way, they will easily produce higher-order aberrations.

SUMMARY OF THE INVENTION

It is an object of the present invention to provide a spherical aberration corrector which is for use in an electron microscope and which permits the magnification to be varied by means of spherical aberration correction optics. Furthermore, the corrector can correct the rotational relation between multipole elements within a plane perpendicular to the optical axis without varying the phase angles of the multipole elements. For this purpose, the spherical aberration corrector built in accordance with the present invention has a rotation-correcting lens between two axially symmetric lenses located between the two multipole elements. This corrector is characterized in that the rotation-correcting lens is positioned within the focal plane of an electron trajectory formed between the axially symmetric lenses to rotate electrons within the plane perpendicular to the optical axis.

The invention also provides a spherical aberration corrector which is for use in an electron microscope and has two axially symmetric lenses (i.e., a front-stage lens having a focal length of $f_1$ and a rear-stage lens having a focal length of $f_2$ different from $f_1$, i.e., $f_1 \neq f_2$) between two multipole elements (i.e., a front-stage multipole element and a rear-stage multipole element), the corrector being designed such that the distance between the front-stage multipole element and the front-stage lens is set to $f_1$, the distance between the two axially symmetric lenses is set to $f_1+f_2$, the distance between the rear-stage lens and the rear-stage multipole element is set to $f_2$, the excitation intensity of the front-stage multipole element is set to $K_1$, and the excitation intensity of the rear-stage multipole element is set to $K_2$. The lengths of the front-stage and rear-stage multipole elements as measured along the optical axis are $Z_1$ and $Z_2$, respectively. The corrector is further characterized in that it is designed to satisfy the relations $$Z_2 = a^2 Z_1$$

$$K_2 = \frac{K_1}{a^5}$$

where $a = \frac{f_2}{f_1}$

Other objects and features of the present invention will appear in the course of the description thereof, which follows.

DESCRIPTION OF THE PREFERRED EMBODIMENTS

Figure 1:
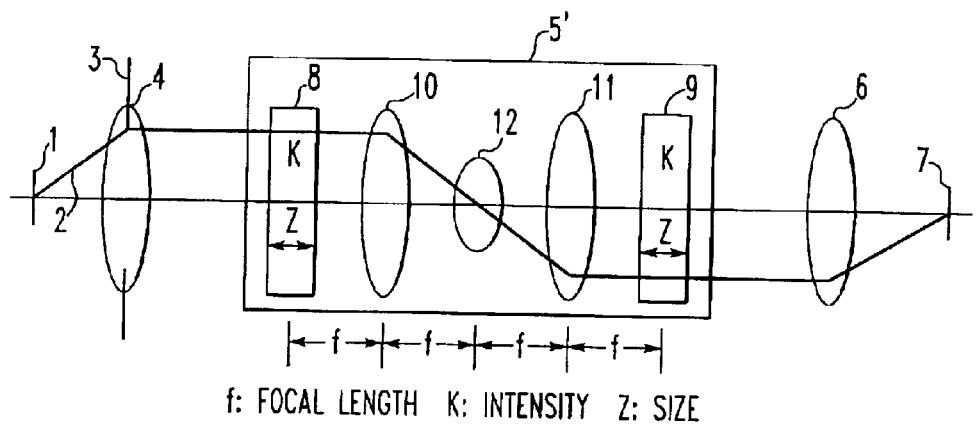
FIG. 1 is a ray diagram of a spherical aberration corrector for use in an electron microscope, the corrector being built according to the present invention.
Figure 3:
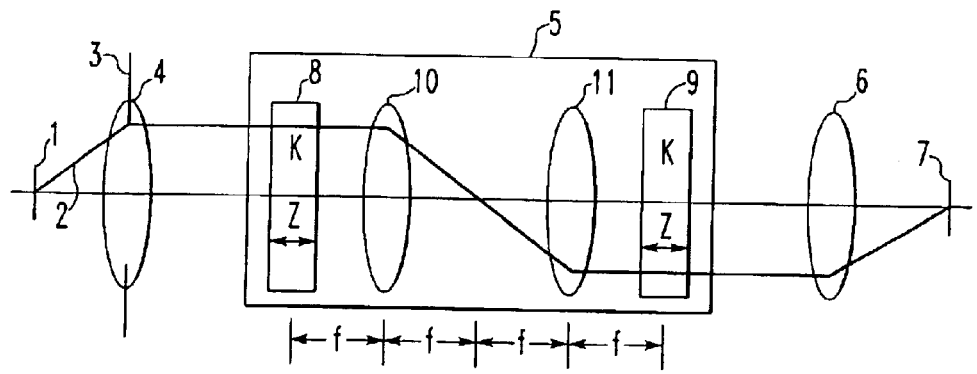
FIG. 3 is a ray diagram schematically showing the illumination system of an electron microscope, illustrating the prior art method of correcting spherical aberration.

Referring to FIG. 1, there is shown a spherical aberration corrector according to a first embodiment of the present invention, the corrector being for use in an electron microscope. Like components are indicated by like reference numerals in both FIGS. 1 and 3. The present embodiment is characterized in that a rotation-correcting lens 12 is placed within the focal plane of an electron trajectory formed between the axially symmetric lenses 10 and 11 to prevent the multipole elements 8 and 9 from having a rotational relation about the electron trajectory.

The electron beam 2 emitted from the source 1 passes through the condenser lens 4 having the aperture 3 and is made parallel to the optical axis. Then, the beam enters spherical aberration correction optics 5'. An electron beam leaving the aberration correction optics 5' parallel to the optical axis is directed onto the specimen 7 through the objective lens 6. In the same way as in FIG. 3, the lenses 10 and 11 of the spherical aberration correction optics 5' have the same focal length of f. The distance between the multipole element 8 and the axially symmetric lens 10 is set to f. The distance between the lenses 10 and 11 is set to 2 f. The distance between the lens 11 and the multipole lens 9 is set to f. The multipole elements 8 and 9 are excited with the same magnitude K. The elements 8 and 9 have the same width Z as measured along the optical axis. The multipole elements 8 and 9 are so arranged that there is no rotational relation about the optical axis within a plane perpendicular to the optical axis.

The spherical aberration correction optics 5' have the rotation-correcting lens 12 positioned within the focal plane of the electron trajectory formed between the axially symmetric lenses 10 and 11, which, in turn, are disposed between the multipole elements 8 and 9 for producing hexapole fields. Since the correcting lens 12 is placed within the focal plane, the electron beam travels across the optical axis. Consequently, the rotation-correcting lens 12 does not converge the electron beam. However, the lens 12 can rotate the electron beam by using a magnetic lens as the rotation-correcting lens 12. In this way, the main action of the rotation-correcting lens 12 on electrons is to rotate them within a plane perpendicular to the optical axis rather than to converge them. At this time, the angle of rotation is in proportion to the magnetic lens current.

Therefore, if the multipole elements 8 and 9 somewhat angularly deviate from the electron trajectory due to manufacturing and assembly tolerances, the introduced rotational relation can be corrected by varying the current of the rotation-correcting lens 12 instead of controlling the phase angles of the multipole elements as in the prior art. In consequence, generation of detrimental higher-order aberrations accompanying phase control of the multipole elements can be prevented.

Figure 2:
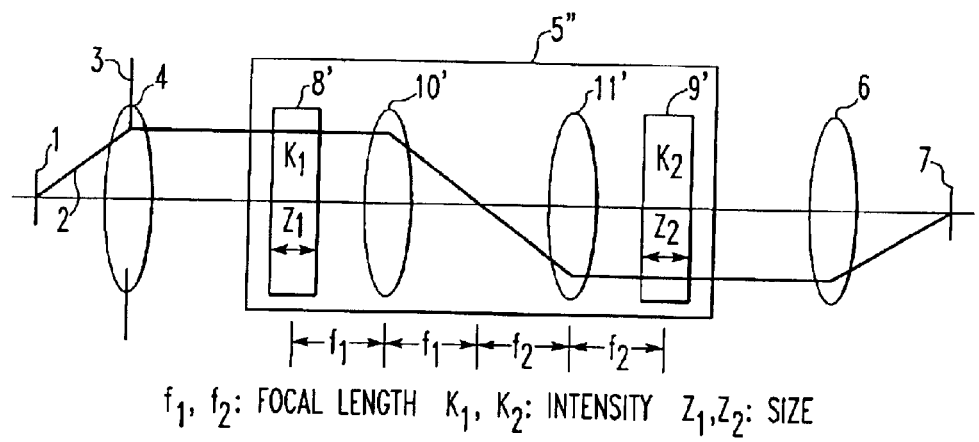
FIG. 2 is a ray diagram similar to FIG. 1, but showing another spherical aberration corrector according to the present invention.

FIG. 2 is a diagram illustrating a second embodiment of the present invention. Note that like components are indicated by like reference numerals in various figures including FIGS. 1, 2, and 3. Aberration correction optics 5" of the present embodiment have two axially symmetric lenses 10' and 11' having focal lengths of $f_1$ and $f_2$, respectively. The distance between a multipole element 8' and the axially symmetric lens 10' is set to $f_1$. The distance between the two axially symmetric lenses 10' and 11' is set to $f_1+f_2$. The distance between the axially symmetric lens 11' and the multipole element 9' is set to $f_2$. The excitation intensity of the multipole element 8' is set to $K_1$. The excitation intensity of the multipole element 9' is set to $K_2$. The widths (dimensions as measured along the optical axis) of the multipole elements 8' and 9' are set to $Z_1$ and $Z_2$, respectively. The multipole elements are operated to produce hexapole fields in the same way as in the prior art technique.

Analytical calculation shows that the tilt R of the electron trajectory at the time when electrons leave the correction optics 5", the tilt being produced by passage through the correction optics 5", is given by:

$$R = r^2(\cos 3\theta)\left(K_1 Z_1\left(\frac{f_1}{f_2}\right) - K_2 Z_2\left(\frac{f_2}{f_1}\right)^2\right) + \tag{1}$$
$$r^3\left(K_1^2 Z_1^3\left(\frac{1}{3}\right)\left(\frac{f_1}{f_2}\right) + K_2^2 Z_2^3\left(\frac{1}{3}\right)\left(\frac{f_1}{f_2}\right)^3\right) -$$
$$K_1 K_2 Z_2 Z_1\left(\frac{f_2}{f_1}\right)^2 r^3(\cos 3\theta)^2\left(Z_2\left(\frac{f_1}{f_2}\right)^2 - Z_1\right)$$

where r is the distance of the electron trajectory from the optical axis, the trajectory being incident parallel to the optical axis.

Figure 4:
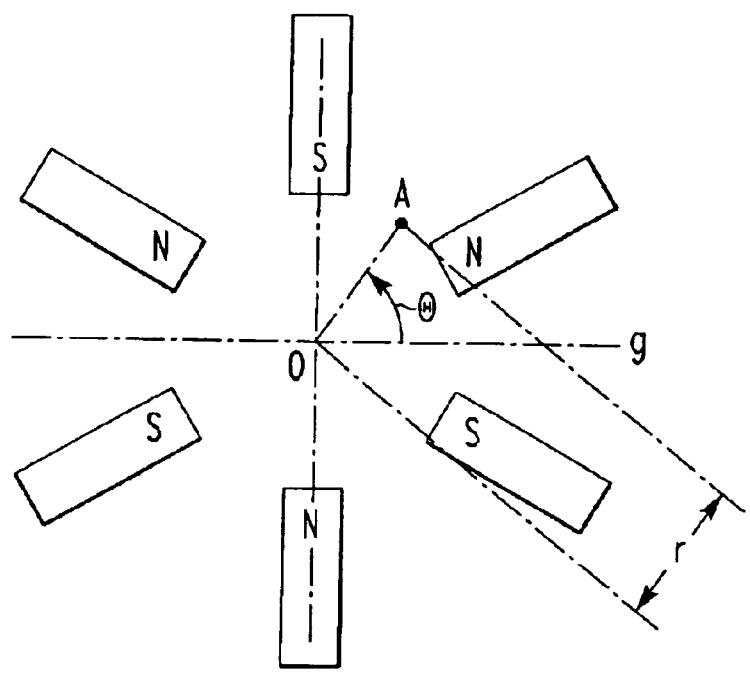
FIG. 4 is a diagram illustrating parameters r and θ in an aberration corrector.

FIG. 4 illustrates distance r and angle θ where hexapole elements are used as multipole elements. This figure is a cross-sectional view taken through the multipole element 8' normal to the optical axis, O. Electrons enter the multipole element 8' at position A. A direction indicated by g forms a reference when rotation about the optical axis is considered. The distance from the optical axis O is indicated by r. The angle from the reference direction g is indicated by θ and shows the direction of the position A when electrons enter the multipole element 8'.

The first term of Eq. (1) above indicates second-order aberration with three-fold symmetry. This term should be made zero in order to form a very fine electron probe. The second term of Eq. (1) indicates three-order aberration (−δ) with axial symmetry produced by the spherical aberration correction optics 5". This aberration (−δ) is used to cancel the spherical aberration (δ) of the illumination system of the electron microscope. The third term of Eq. (1) indicates third-order aberration with six-fold symmetry. This term should be made zero in order to form a very fine electron beam. Accordingly, conditions for achieving spherical aberration correction are given by $$K_1 Z_1\left(\frac{f_1}{f_2}\right) - K_2 Z_2\left(\frac{f_2}{f_1}\right)^2 = 0 \tag{2}$$

$$r^3\left(K_1^2 Z_1^3\left(\frac{1}{3}\right)\left(\frac{f_1}{f_2}\right) + K_2^2 Z_2^3\left(\frac{1}{3}\right)\left(\frac{f_1}{f_2}\right)^3\right) = -\delta \tag{3}$$

$$Z_2\left(\frac{f_1}{f_2}\right)^2 - Z_1 = 0 \tag{4}$$

where δ is the variation (proportional to $r^3$) in the tilt of the trajectory due to spherical aberration. $K_1$ and $K_2$ indicating the intensities of hexapole fields are proportional to the current flowing through the multipole elements. We now assume that $$a = \frac{f_2}{f_1} \tag{5}$$

Then, Eqs. (2) and (4) are respectively changed into the forms $$Z_2 = a^2 Z_1 \tag{6}$$

$$K_2 = \frac{K_1}{a^5} \tag{7}$$

In the conventional spherical aberration corrector, the relations $f_1=f_2$, $Z_2=Z_1$, and $K_1=K_2$ hold provided that a=1.

Therefore, Eqs. (4) and (2) naturally assume a value of 0. The corrector corrects the spherical aberration by means of $K_1$ (=$K_2$) determined by Eq. (3).

On the other hand, in the present invention, the focal distances $f_1$ and $f_2$ of the axially symmetric lenses 10' and 11', respectively, are set to different values. The requirement of Eq. (4) for these different values inevitably determines the relation between the widths $Z_1$ and $Z_2$. The relation between the excitation intensities $K_1$ and $K_2$ is inevitably determined from the relation between the focal distances $f_1$ and $f_2$, the relation between the widths $Z_1$ and $Z_2$, and the relation given by Eq. (2). Finally, the requirement of Eq. (3) determines the values of the widths $Z_1$ and $Z_2$. Thus, the spherical aberration is corrected. In the present invention, the ratio between the focal lengths $f_1$ and $f_2$ can be set at will. Consequently, the magnification of the electron trajectory can be varied by the correction system. Where the image is focused at infinity, the function of a lens having a magnification of 1/a can be imparted to the correction optics.

Figure 5:
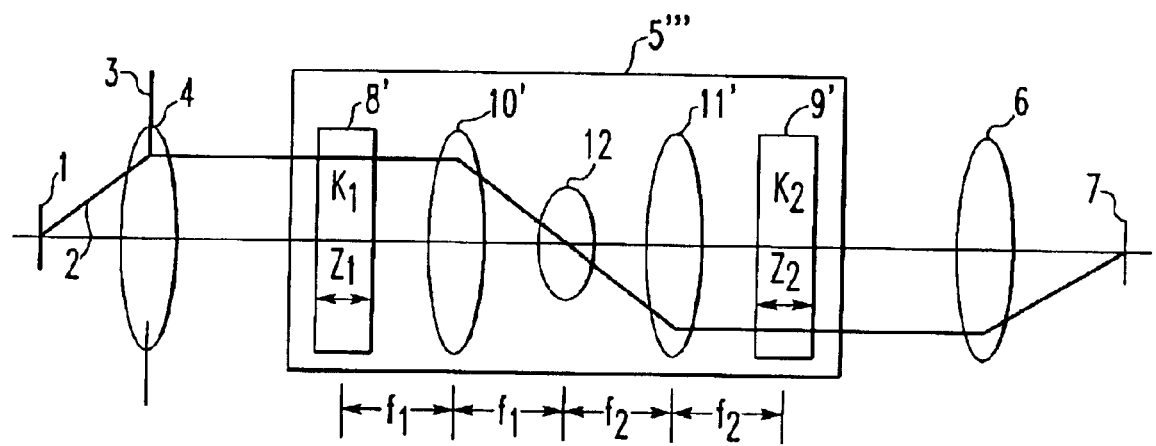
FIG. 5 is a ray diagram similar to FIGS. 1 and 2, but showing a further spherical aberration corrector according to the present invention.

Obviously, the rotation-correcting lens 12 of the first embodiment can be applied to the case of the second embodiment. As shown in FIG. 5, if the multipole elements 8' and 9' are rotated relative to the electron trajectory, the rotation can be corrected by placing the rotation-correcting lens 12 within the focal plane of the electron trajectory formed between the axially symmetric lenses 10' and 11' of aberration corrector 5'".

In the embodiment above, a spherical aberration corrector for use with the illumination system of an electron microscope has been described in connection with FIGS. 1–3 and 5, where a source 1, condenser lenses 4, an objective lens 6, and a specimen 7 are shown. This spherical aberration corrector can be effectively used as a spherical aberration corrector for use with the imaging system of the electron microscope. In particular, referring again to FIGS. 1–3 and 5, the spherical aberration corrector for use with the imaging system can be similarly operated if the following conditions are established. Indicated by 1 is a specimen. Indicated by 4 is an objective lens of the imaging system. Indicated by 6 is the first intermediate lens of the imaging system. Indicated by 7 is an image plane formed by the first intermediate lens 6. An example of application of the inventive spherical aberration corrector to an electron microscope is described below by referring to FIG. 6.

Figure 6:
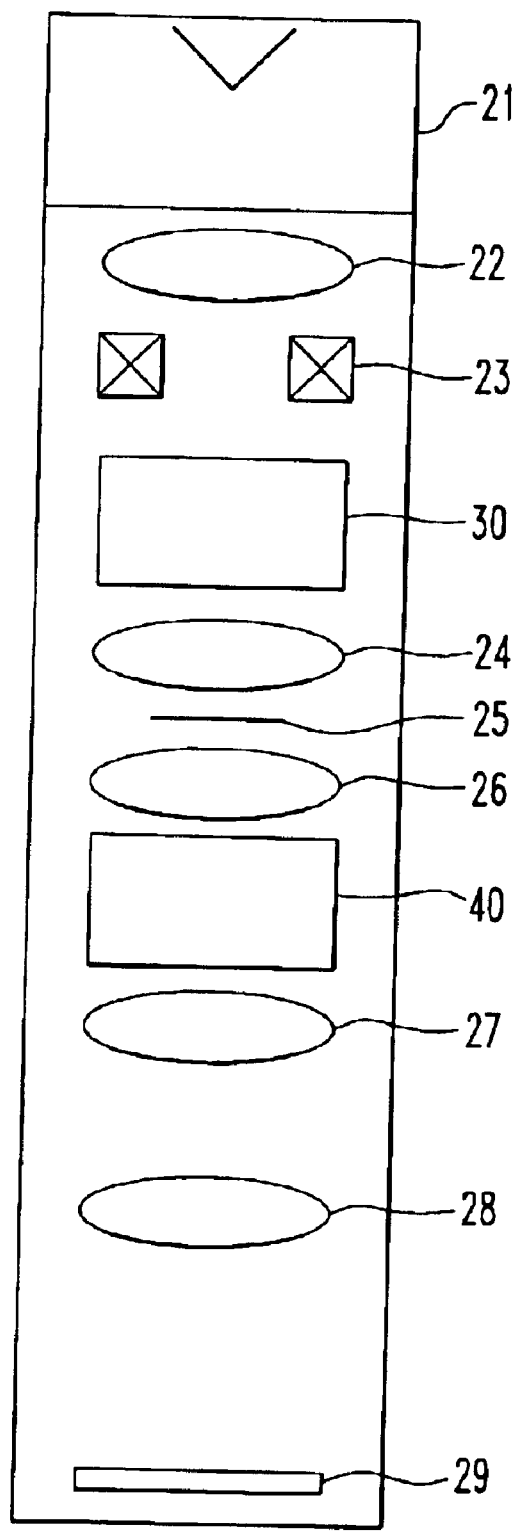
FIG. 6 is a schematic diagram illustrating an example in which a spherical aberration corrector according to the present invention is applied to an electron microscope.

FIG. 6 shows a case in which the inventive spherical aberration corrector is used in an electron microscope, which has an electron gun 21 for producing an electron beam and giving a desired energy to the beam. A system of condenser lenses 22 is made up of plural lenses for focusing the electron beam. A deflector 23 deflects and scans the electron beam in two dimensions. An objective lens 24 directs the beam onto a specimen 25. These electron optical elements 21–24 constitute an electron optical system that is also referred to as the illumination system.

In this illumination system, there are some methods of directing the electron beam onto the specimen 25. In a first method, the beam is focused sharply and directed at a desired position on the specimen 25. In a second method, the beam is focused sharply and scanned across a desired region on the specimen 25 in two dimensions, using the deflector 23. In a third method, the electron beam is neither focused sharply nor scanned. A uniform electron beam having the same size as the desired area on the specimen 25 is directed at the desired area.

Referring still to FIG. 6, an objective lens 26 directs the electron beam onto the specimen 25, for example, where the third method as described above is implemented. The objective lens 26 magnifies a transmitted electron image or TEM image of the beam transmitted through the specimen 25. A system of intermediate lenses 27 consists of a plurality of lenses for further magnifying the TEM image magnified by the objective lens 26. A projector lens 28 projects the magnified TEM image onto a fluorescent screen 29. An electron optical system made of the components 26–29 is herein referred to as the imaging system. The electron gun 21 and the following components are all placed in a vacuum environment. In the above description, for the sake of illustration, there are two objective lenses 24 and 26. Usually, a single lens can act as the objective lens 24 and also as the objective lens 26.

Referring still to FIG. 6, a spherical aberration corrector 30 is built where one of the spherical aberration correctors 5', 5", and 5'" of the invention is applied to the illumination system. A spherical aberration corrector 40 is built where any one of the spherical aberration correctors 5', 5", and 5'" of the invention is applied to the imaging system. The spherical aberration corrector 30 corrects the aberration of the focused electron beam by the first and second illumination methods for the illumination system. Thus, a finer electron probe is obtained. The spherical aberration corrector 40 corrects the aberration of the objective lens 26 or the imaging system by the third illumination method for the illumination system, thus obtaining a magnified image at a higher resolution.

As described thus far, the present invention can achieve the following advantage to begin with.

(1) Rotational relation within a plane perpendicular to the optical axis between two multipole elements forming a spherical aberration corrector can be corrected without varying the phase angles of the multipole elements. Therefore, higher-order aberrations that would normally be produced by variations in phase of the multipole elements can be prevented.

Furthermore, where the invention is applied to the illumination system of an electron microscope, the following advantages can be derived.

(2) Since the spherical aberration of the illumination system can be corrected, a very fine electron probe can be obtained. This permits characteristic X-ray analysis of a microscopic area. Also, high-resolution imaging for scanning images, such as secondary electron images and scanning transmitted electron images is enabled.

(3) The spherical aberration corrector can also play some intrinsic role of the illumination system designed as a multiple-stage demagnification system.

Where the present invention is applied to the imaging system of an electron microscope, the following advantages can be had.

(4) Since the spherical aberration of the imaging system can be corrected, high-resolution TEM imaging is enabled.

(5) Some of intrinsic roles of the imaging system designed as a multiple-stage magnification system can be assigned to the spherical aberration corrector.

Having thus described my invention with the detail and particularity required by the Patent Laws, what is desired protected by Letters Patent is set forth in the following claims.

The invention claimed is:

1. A spherical aberration corrector for use in an electron microscope, comprising:

two multipole elements;

two axially symmetric lenses placed between said two multipole elements; and a magnetic rotation-correcting lens placed in a focal plane of an electron trajectory formed between said axially symmetric lenses, said magnetic rotation-correcting lens acting to mainly rotate electrons within a plane perpendicular to an optical axis.

2. A spherical aberration corrector for use in an electron microscope, comprising:
   a front-stage multipole element excited with an intensity of $K_1$ and having a length of $Z_1$ as measured along an optical axis;
   a rear-stage multipole element excited with an intensity of $K_2$ and having a length of $Z_2$ as measured along the optical axis;
   a first axially symmetric lens forming a front-stage lens and having a focal length of $f_1$, said front-stage lens being located at a distance of $f_1$ from said front-stage multipole element; and
   a second axially symmetric lens forming a rear-stage lens and having a focal length of $f_2$ different from (i.e., $f_1 \neq f_2$) said first and second axially symmetric lenses being disposed between said front-stage multipole element and said rear-stage multipole element, said first and second axially symmetric lenses being spaced from each other at a distance of $f_1 \neq f_2$, said rear-stage lens being located at a distance of $f_2$ from said rear-stage multipole element;

wherein $$Z_2 = a^2 Z_1$$

$$K_2 = \frac{K_1}{a^5}$$

where $a = \frac{f_2}{f_1}$.

3. A spherical aberration corrector for use in an electron microscope as set forth in claim 2, wherein a rotation-correcting lens is positioned within a focal plane of an electron trajectory formed between the two axially symmetric lenses to rotate electrons within a plane perpendicular to the optical axis.

* * * * *

UNITED STATES PATENT AND TRADEMARK OFFICE
CERTIFICATE OF CORRECTION

PATENT NO. : 6,836,373 B2
DATED : December 28, 2004
INVENTOR(S) : Hosokawa

It is certified that error appears in the above-identified patent and that said Letters Patent is hereby corrected as shown below:

Title page,
Item [30], Foreign Application Priority Data, delete the first reference:
"Nov. 16, 2000(JP)   2000-349222"

Column 7,
Line 18, "from (i.e., $f_{1 \neq f2}$)" should read -- from (i.e., $f_1 \neq f_2$) --

Column 8,
Line 1, "distance of $f_1 \neq f_2$" should read -- distance of $f_{1+}f_2$ --

Signed and Sealed this

Twenty-first Day of June, 2005

JON W. DUDAS
*Director of the United States Patent and Trademark Office*